United States Patent [19]

Ruzicka et al.

[11] 4,315,754
[45] Feb. 16, 1982

[54] FLOW INJECTION ANALYSIS WITH INTERMITTENT FLOW

[75] Inventors: Jaromir Ruzicka, Copenhagen; Elo H. Hansen, Lyngby, both of Denmark

[73] Assignee: Bifok AB, Sollentuna, Sweden

[21] Appl. No.: 70,658

[22] Filed: Aug. 28, 1979

[51] Int. Cl.³ .................... G01N 35/08; G01N 33/14; G01N 33/66
[52] U.S. Cl. .................................. 23/230 R; 23/901; 73/61.1 C; 422/81
[58] Field of Search ......................... 23/230 R, 230 A; 422/64, 65, 68, 81, 82; 73/425.4 R

[56] References Cited

U.S. PATENT DOCUMENTS

| | | | |
|---|---|---|---|
| 3,690,833 | 9/1972 | Ferarri | 422/82 |
| 3,908,702 | 9/1975 | Klosse et al. | 23/230 R |
| 4,009,999 | 3/1977 | Negersmith | 422/82 |
| 4,022,575 | 5/1977 | Hansen et al. | 422/81 X |
| 4,049,381 | 9/1977 | Burns et al. | 422/82 |

Primary Examiner—Michael S. Marcus
Attorney, Agent, or Firm—Poms, Smith, Lande & Rose

[57] ABSTRACT

Continuous flow analysis with an unobstructed, unsegmented carrier stream transporting a sample plug through a main conduit from a sample injection station to a flow-through detector. One or more reagents are injected in the sample plug on its way through the main conduit, the dispersion being controlled to optimize the conditions of chemical reaction. The reagents are added by being pumped in intermittently in merging streams, at least one of the solution delivering devices being activated and deactivated at pre-programmed time intervals during each sampling cycle. Each cycle is initiated by injecting the sample solution at the sample injection station. The solution delivering devices can have various pumping rates and at least one pump may be an automatic burette. The delivery is controlled by a timer or microcomputer, and the transport of solution can be momentarily stopped before the sample plug enters or while it is inside the flow-through detector.

7 Claims, 9 Drawing Figures

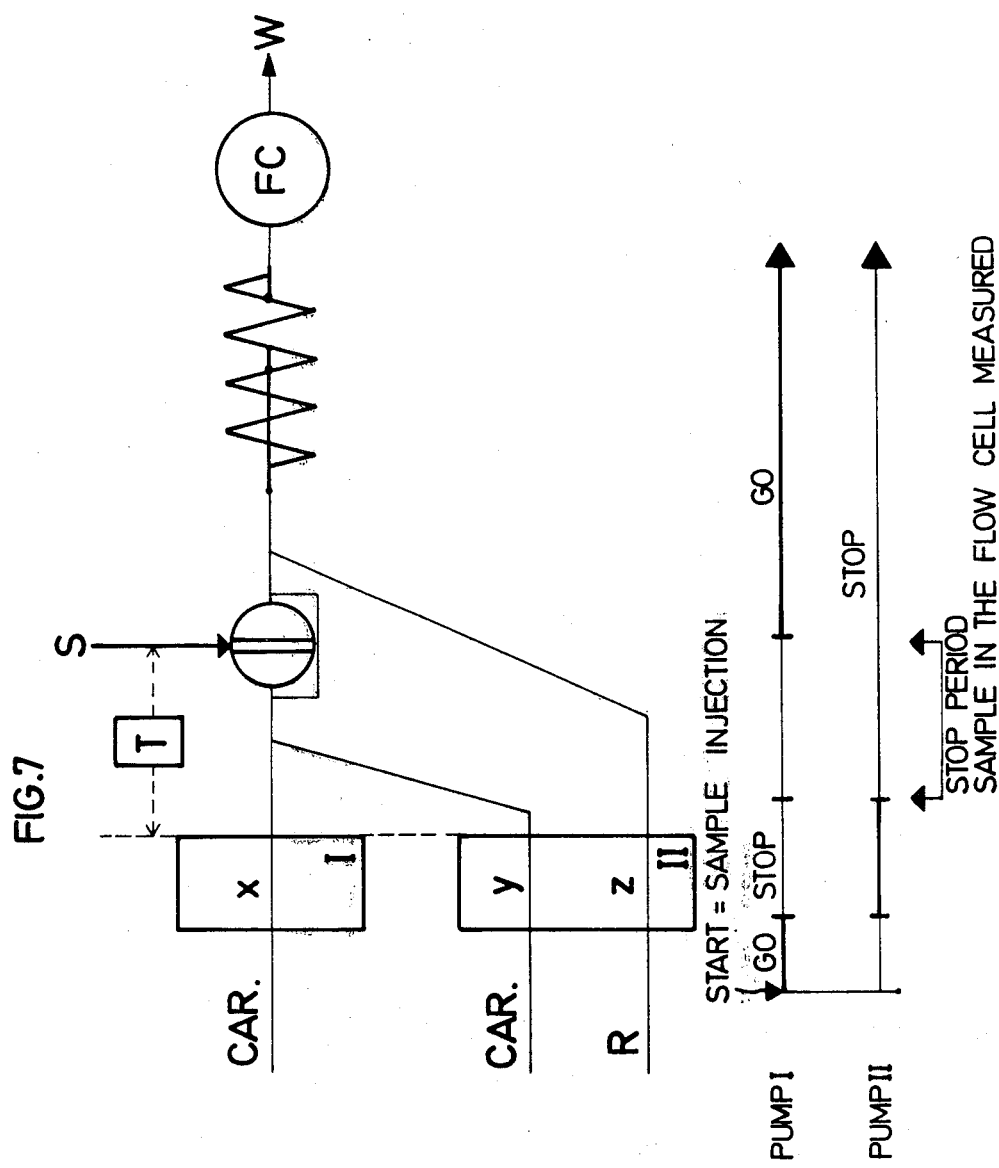

FLOW INJECTION ANALYSIS WITH INTERMITTENT FLOW

Flow injection analysis, FIA, has opened up new areas within the field of analysis. FIA is a continuous analysis system in which discrete volumes of sample solution are successively injected into a continuous, unobstructed carrier stream. The sample solutions react with the carrier stream and a detector for registering the results of the reactions is placed downstream from the point of injection. The principles for FIA are described in detail in our U.S. Pat. No. 4,022,575.

One of the most important developments of the FIA theory (see our U.S. Patent Application Ser. No. 48,002, filed June 13, 1979, Stop-Flow) increases the residence time by decreasing the velocity of the carrier stream instead of increasing the length of the reaction coil, because lengthening of the sample zone path leads to increased dispersion, while decrease of the pumping rate results in lesser spreading of the sample zone. Should, however, the carrier stream cease to move, the dispersion of the sample zone will stop (except for a negligible contribution due to molecular diffusion) and the dispersion, $D_t$, will become independent of time. Thus by applying intermittent pumping, one can gain reaction time during the stop interval when the carrier stream does not move. If the sample zone is stopped within the flow cell itself, it is possible to record the change of, say, optical density, caused by the reaction between the sample component and the reagent in the carrier stream. The obvious prerequisite for such a reaction rate measurement to be successful is that the movement of the carrier stream be able to be exactly controlled from the operational pumping rate used to complete standstill, and that always the same section of the sample zone be able to be reproducibly held within the flow cell for measurement. In practice, this is best achieved by using an electronic timer which is activated by a microswitch connected to the injection valve. Thus any delay time as well as any length of stop time can be chosen so that it suits the reaction rate of the particular chemistry.

The invention will now be described in more detail with reference to the accompanying drawings, of which FIG. 1 is a comparison between continuous FIA and stop-flow, FIG. 2 is a modified stop-flow system, FIG. 3 is a graph concerning the system according to FIG. 2.

FIG. 7 shows merging zones with intermittent pumping,

Figure 1:
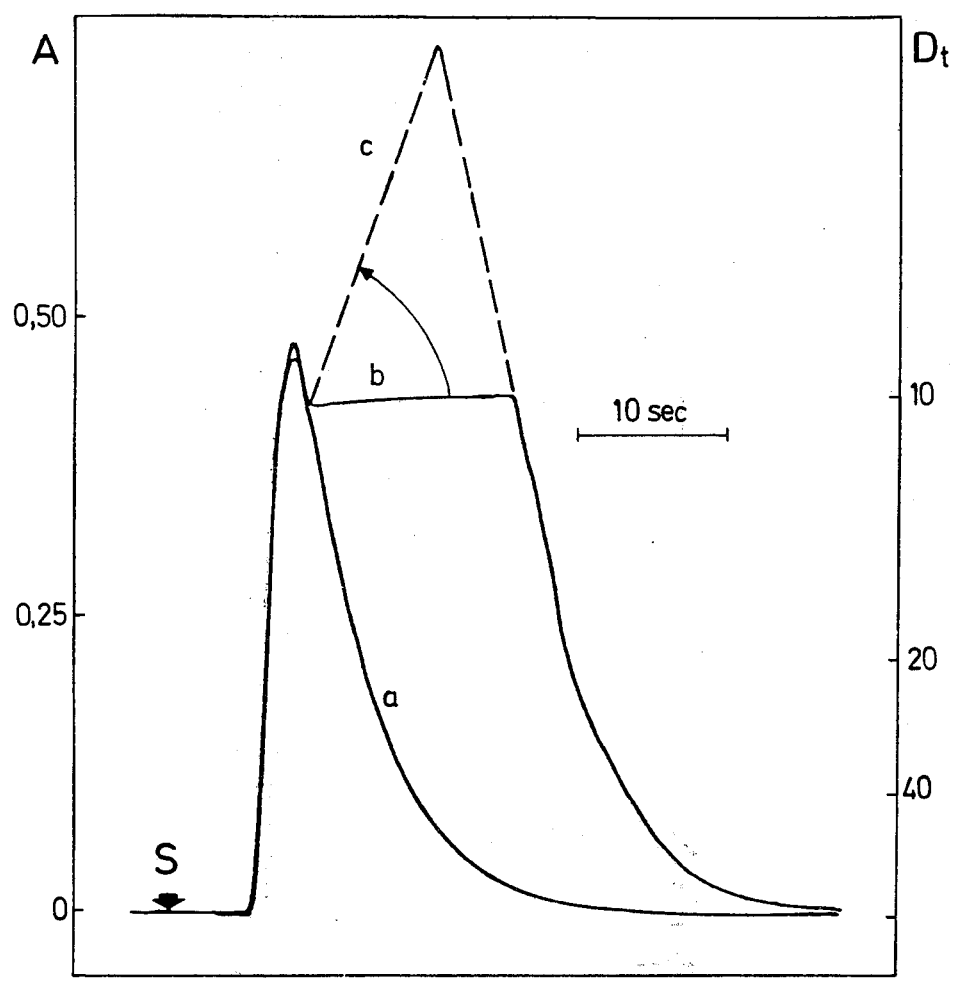

FIG. 1 demonstrates the principles of the Stop-Flow FIA method. A dyed sample zone is injected into a colourless carrier stream and the absorbance is recorded by means of a colorimetric flow-through cell. All curves are recorded from the same point (S) by injecting 26 microliters of the same dye. Curve a shows continuous pumping, curve b 9 seconds of pumping, 14 seconds stop and continuous pumping again, and curve c, the dotted line, indicates the curve which would have been registered if any chemical reaction had taken place within the flow cell during the 14 second stop interval.

Reaction speed measurements are often used within clinical chemistry and therefore the enzymatic determination of glucose based on the use of glucose hydrogenase coupled to the spectrophotometric measurement of the coenzyme AADH became the first use of the Stop-Flow FIA system.

Another interesting example is the determination of $SO_2$ in wine, based on the well-known West-Gaeke method in which a pink-coloured compound, formed by the reaction between pararosaniline and sulphur dioxide and catalyzed by formaldehyde, is measured at 580 nm. While the determination of sulphur dioxide (which is always present in wine as a preservative) can be performed on samples of white wine by a simple direct measurement; the colour of red wines interferes, especially because for different coloured wines it presents a variable blank. This, however, can be corrected in each individual sample by measuring the increase of absorbance due to the reaction between sulphur dioxide and pararosaniline while the sample zone is kept still within the flow-through cell (cf. FIG. 1).

Figure 2:
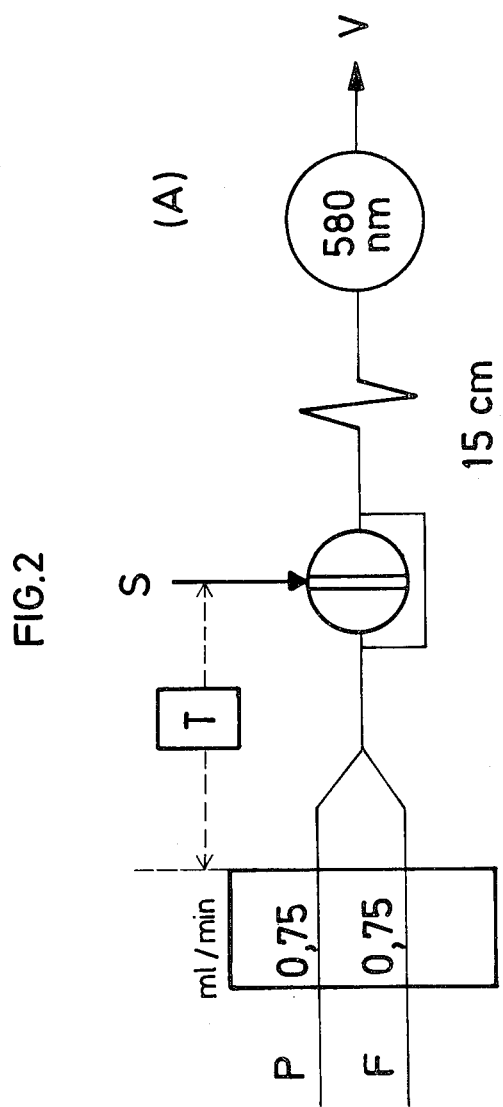

Since the premixed reagent is not stable and changes with time, the simplest stop-flow system had to be slightly modified (FIG. 2).

The sample (10 $\mu$l) is injected into a carrier solution of pararosaniline (0.08% in 0.3 M $H_2SO_4$) to which is added a solution of formaldehyde (0.5% in 0.3 M $H_2SO_4$) which catalyses the colour-forming reaction. After mixing of the reagents in the 15 cm (0.5 mm I.D.) coil, the sample zone is, by means of the electronic timer, stopped in the flow-through cell of the spectrophotometer. This testing arrangement permitted the determination of sulphur dioxide in wines at a rate of 105 samples per hour and with the analytical readout available 23 seconds after sample injection.

Figure 3:
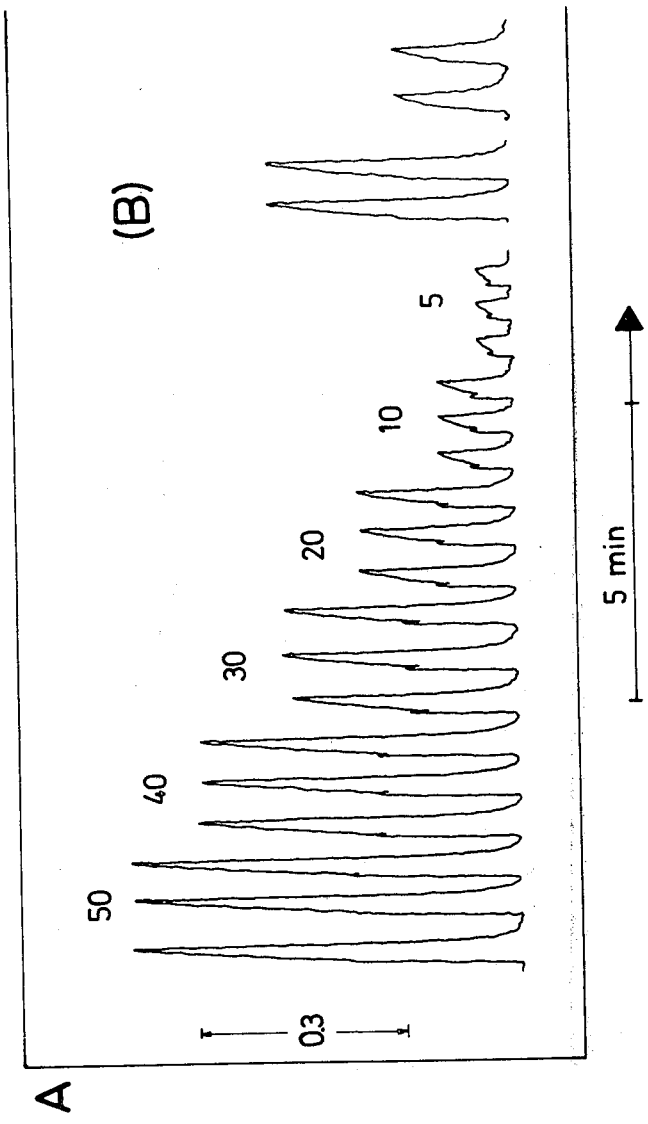
Figure 4:
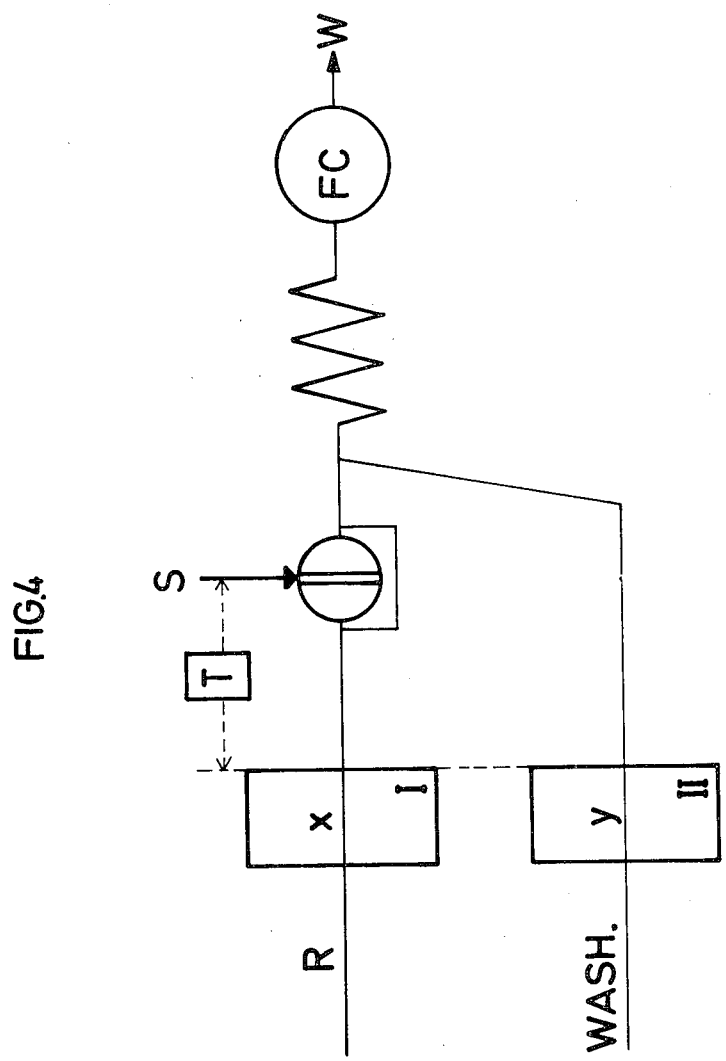
FIG. 4 is the intermittent system according to the invention.
Figure 5:
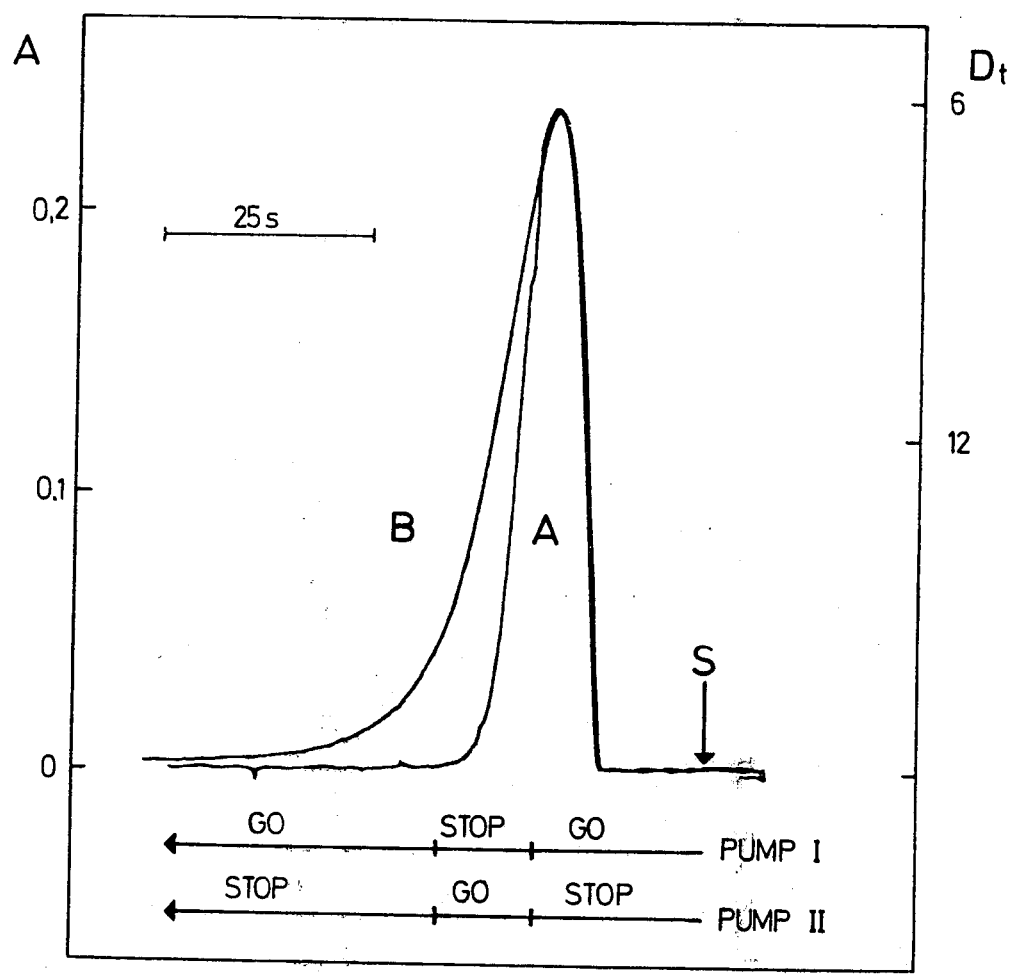
FIG. 5 is a graph illustrating the system according to FIG. 4.
Figures 6A, 6B:
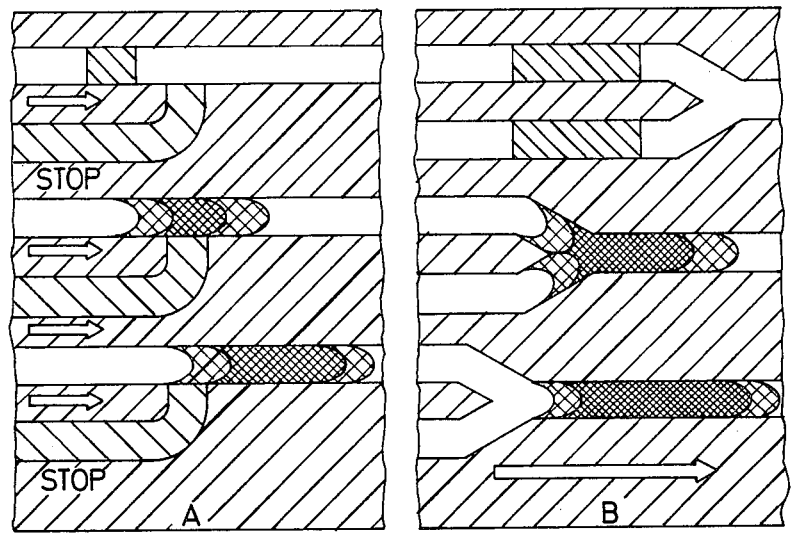
FIG. 6 shows merging zones.
Figure 8:
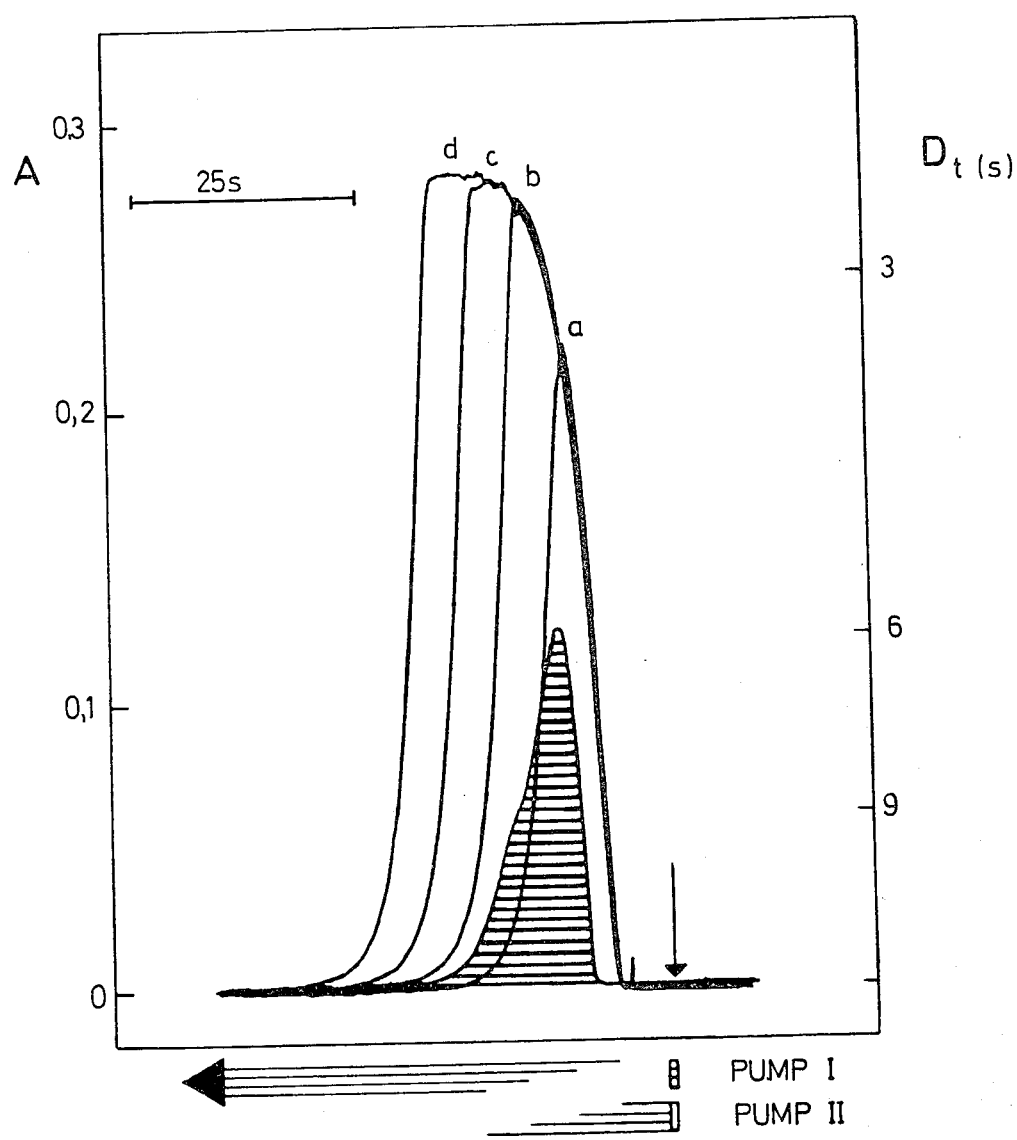
FIG. 8 illustrates the system according to FIG. 7.

FIG. 3 shows the calibration record for sulphur dioxide using the stop-flow system in FIG. 2. The concentrations are given in ppm $SO_2$. The delay time was chosen slightly longer than the residence time, i.e., the samples were stopped shortly after the peak maxima had been passed. As the stop time was identical in all cases (15 sec.), the analytical result is given as the peak increase during the stop interval. To the right are shown the records for the determination of the free sulphur dioxide contents in two white wines, Touraine Blanc, 29 ppm; and Gumpoldskirschner, 1977, 18 ppm.

It is interesting to note that stop-flow injection analysis can be performed on the various sections of the dispersed sample zone i.e., not only by monitoring that part corresponding to the peak maximum, but by stopping in the flow cell any segment on the tailing portion. This is described in detail in our U.S. Patent Application Ser. No. 48,002, filed June 13, 1979, Stop-Flow.

Figure 9:
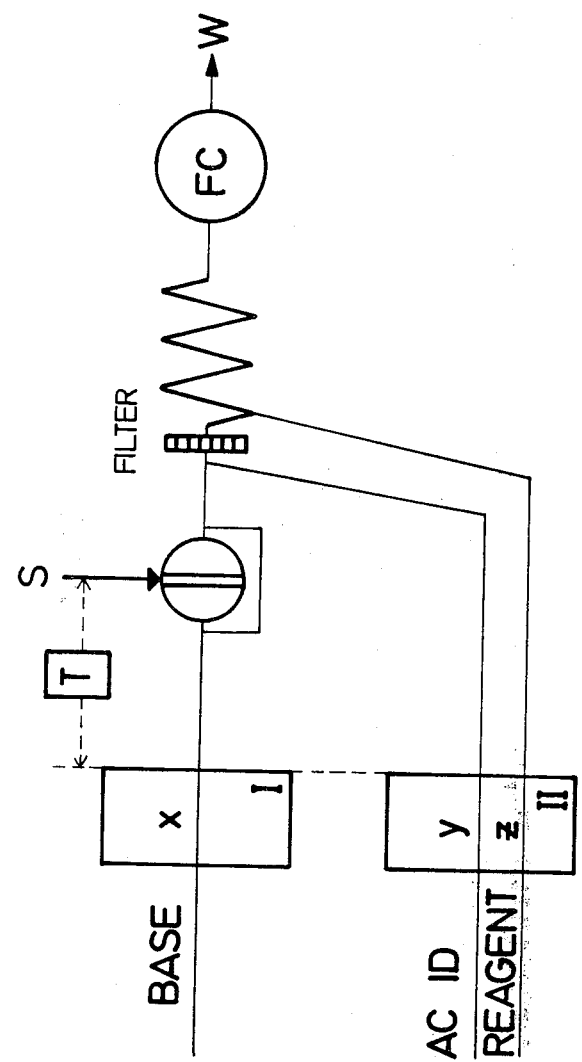
FIG. 9 shows the intermittent addition of two or more reagents to a sample.

Thus, in contrast to conventional stop-flow systems in which sample and reagent solutions are completely mixed by force in a special chamber, the stop-flow injection method readily allows adjustment to obtain optimum measurement conditions. Also, since the mixing takes place in a simple tubing without special auxiliaries, the apparatus is simple to construct, and since during the stop period no reagent is being pumped, the stop-flow method is less demanding on reagent consumption than the continuous flow approach. It should, however, be pointed out that if the rate of the sample zone dispersion were slower than the rate of the chemiwhich peak one after the other. This can be done, for example, by precipitating out two or more metals as hydroxides by adding a weakly acid or neutral sample containing the dissolved components, for example Cu, Pb and Cd, to a flowing liquor, e.g. 0.001 M NaOH and filtering out the precipitant by allowing pump I to run for a sufficiently long time to wash out the sample zone. Then pump II is started with the addition of a diluted acid which gradually dissolves the hydroxides. The plan for the apparatus is shown in FIG. 9.

Cd never precipitated, and the diluted acid first dissolves Pb and then Cu, so that the metal ions will pass through the filter and form a colour with the reagent to then be measured spectrophotometrically. Alternatively, a conductivity detector can be used if the reagent is a base exactly equimolar with the acid and the pumping rate y is exactly equal to z, because the change of conductivity will follow the amount of acid necessary to dissolve the hydroxide. This is a widely applicable principle. Finally, it should be pointed out that although this might seem to resemble chromatography, it is not; since the components to be separated form a solid second phase which is dissolved during each measuring cycle.

The merging zone concept might, if applied to a wider range of enzymatic assays, reverse the present trend towards the use of insolubilized enzymes, not only because of the high sampling rate and instant response of the FIA system, but also because rate measurements and blanking are not so readily accomplished in systems where enzymes are fixed in the form of columns or tubes.

The drawback of the merging zones approach is that a variable baseline signal will affect the measurement in an unfavourable way if the injected reagent zone alone is sensed by the flow-through detector. Thus in spectrophotometry the reagent should be colourless or at least should not absorb significant amounts at the wavelength at which the reaction product is being monitored. A very interesting aspect of the merging zones approach is the great versatility of this approach when performed by means of intermittent pumping. By choosing different lengths of reagent zone, one can obtain individual blanks for the reagent alone, the sample alone as well as the rate of formation of the reaction product.

What we claim is:

1. A method of analyzing a material within a flowing liquid carrier, comprising the steps of:
    (a) forming an entirely liquid flowing carrier stream;
    (b) injecting a discrete, well-defined liquid sample portion into said carrier;
    (c) introducing at least one reagent in the form of a liquid to said sample portion by intermittently activating separate pumps disposed to transport said carrier and said reagent respectively at pre-programmed timed intervals, activation of said pumps being controlled by the step of injecting said sample portion; and
    conducting the combination of said sample and said reagent to a flow-through detector for analysis while controlling dispersion of said sample in said conduit and said detector to optimize desired chemical reactions.

2. The method of claim 1 wherein said method determines the rate of a chemical reaction, said method including the step of stopping the flow of said carrier when said sample is within said flow-through detector and measuring a change in said sample resulting from said reaction within said detector as a function of time.

3. The method of claim 1 including the steps of: operating said pump disposed to transport said carrier at a rate significantly greater that the rate of the pump transporting said reagent; and activating said carrier pump subsequent to a maximum being registered by said detector.

4. The method of claim 1 wherein several reagents are injected into said sample portion.

5. The method of claim 1 including the step of stopping the flow of said carrier when said sample is within said flow-through detector.

6. The method of claim 1 including the step of stopping the flow of said carrier before said sample enters said flow-through detector.

7. The method of claims 1 or 6 including the step of operating said separate pumps to produce significantly different flow rates.

* * * * *